(12) United States Patent
Korman et al.

(10) Patent No.: US 6,171,795 B1
(45) Date of Patent: Jan. 9, 2001

(54) NUCLEIC ACID LIGANDS TO CD40LIGAND

(75) Inventors: Alan J. Korman; Larry Gold, both of Boulder, CO (US)

(73) Assignee: NeXstar Pharmaceuticals, Inc., Boulder, CO (US)

( * ) Notice: Under 35 U.S.C. 154(b), the term of this patent shall be extended for 0 days.

(21) Appl. No.: 09/364,380

(22) Filed: Jul. 29, 1999

(51) Int. Cl.[7] ................................................ C12Q 1/68
(52) U.S. Cl. ....................... 435/6; 435/91.2; 536/23.1; 536/22.1; 536/24.3; 536/24.31
(58) Field of Search ................ 435/6, 375, 325, 435/440; 536/23.1, 24.3, 24.33; 514/44

(56) References Cited

U.S. PATENT DOCUMENTS

| | | | |
|---|---|---|---|
| 5,270,163 | * 12/1993 | Gold et al. .............................. | 435/6 |
| 5,723,323 | 3/1998 | Kauffman et al. ................. | 435/172.3 |
| 5,972,599 | * 10/1999 | Tasset et al. .............................. | 435/6 |
| 6,028,186 | * 10/1999 | Tasset et al. ....................... | 536/24.31 |

FOREIGN PATENT DOCUMENTS

| | | |
|---|---|---|
| 2 183 661 | 6/1987 | (GB) . |
| WO89/06694 | 7/1989 | (WO) . |
| WO 91-19813 | 12/1991 | (WO) . |
| WO92/14843 | 9/1992 | (WO) . |
| 98/130240 | * 7/1998 | (WO) . |

OTHER PUBLICATIONS

Branch Tibs 23 Feb. 1998, p. 45–50.*
Crooke "Antisense Research and Application"p 1–50, Jul. 7 1998.*
Durie et al. (1993) Science 261:1328–1330.
Kirk et al. (1997) Proc. Natl. Acad. Sci. USA 94:8789–8794.
Kirk et al. (1999) Nature Medicine 5:686–693.
Larsen et al. (1996) Nature 381:434–438.
Joyce (1989) Gene 82:83.
Joyce & Inoue (1989) Nucleic Acids Research 17:1711.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Szostak, "Structure and Activity of Ribozymes," *Redesigning the Molecules of Life*, (S.A. Benner, ed.) Springer–Verlag Berline Heidelberg, pp. 87–113, (1988).

* cited by examiner

Primary Examiner—George C. Elliott
Assistant Examiner—Karen A Lacouriere
(74) Attorney, Agent, or Firm—Swanson & Bratschun LLC

(57) ABSTRACT

Methods are provided for generating nucleic acid ligands of CD40ligand. The methods of the invention use the SELEX method for the isolation of nucleic acid ligands. The invention also includes nucleic acid ligands to CD40ligand, and methods and compositions for the treatment and diagnosis of disease using the nucleic acid ligands.

14 Claims, 2 Drawing Sheets

SEQUENCE LISTING

```
<160> NUMBER OF SEQ ID NOS: 33

<210> SEQ ID NO 1
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.  N at position 55
      can be any nucleotide

<400> SEQUENCE: 1
gggaggacga ugcggcucga gaaaggaaca aaggucaacc auccgagccc uaccncagac     60
gacucgcccg                                                            70

<210> SEQ ID NO 2
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 2
gggaggacga ugcggcucga gaaaggaaca aaggucaacc auccgagccc ucccacagac     60
gacucgcccg                                                            70

<210> SEQ ID NO 3
```

```
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 3
gggaggacga ugcggcucga gaaaggaaca aaggucaacc auccgagccc uaccacagac    60
gacucgcccg                                                          70

<210> SEQ ID NO 4
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 4
gggaggacga ugcggcucga gaaaggaaca aaggucaacc auccgagccc aaccucagac    60
gacucgcccg                                                          70

<210> SEQ ID NO 5
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 5
gggaggacga ugcggcucga gaaaggaaca aaggucaacc auccgagccc uaccccagac    60
gacucgcccg                                                          70

<210> SEQ ID NO 6
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(69)
<223> OTHER INFORMATION: All pyrimidines are 2' F.

<400> SEQUENCE: 6
gggaggacga ugcggauuug cgagaaagga gcccucuuaag accaaccauc cgcccagacg   60
acucgcccg                                                           69

<210> SEQ ID NO 7
<211> LENGTH: 70
<212> TYPE: RNA
<213> ORGANISM: Artificial Sequence
```

-continued

```
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 7
gggaggacga ugcggcaaga aaggaacguu cagucaacca ucugcuaccg cuccccagac    60
gacucgcccg                                                          70

<210> SEQ ID NO 8
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 8
gggaggacga ugcggcaaga aaggaacguu cagucaacca ucugcuaccg cccccagac    60 gacucgcccg                                                          70

<210> SEQ ID NO 9
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 9
gggaggacga ugcggagaaa ggaagaacuc ucucaaccau cccacaccag cccccagac    60 gacucgcccg                                                          70

<210> SEQ ID NO 10
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 10
gggaggacga ugcggcaacu cucgagaaag gaaucaucaaa gugucaacca uccgucagac    60
gacucgcccg                                                          70

<210> SEQ ID NO 11
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
```

<220> FEATURE:
<221> NAME/KEY: modified_base
<222> LOCATION: (1)..(70)
<223> OTHER INFORMATION: All pyrimidines are 2' F.

<400> SEQUENCE: 11
gggaggacga ugcggccuaa gaaaggaauu uaaaccaauc aaccaucuag aaccccagac    60
gacucgcccg                                                          70

<210> SEQ ID NO 12
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 12
gggaggacga ugcgggccuc gagaaagaac cauacagggu aaucauccgu ucgcccagac    60
gacucgcccg                                                          70

<210> SEQ ID NO 13
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 13
gggaggacga ucgggucaac cauccaacuc aaguugagaa aggaaccacu agccccagac    60
gacucgcccg                                                          70

<210> SEQ ID NO 14
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 14
gggaggacga ugcggucaac cauccaacuc aaguugagaa aggaaccacu accccagac    60 gacucgcccg                                                          70

<210> SEQ ID NO 15
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)

<223> OTHER INFORMATION: All pyrimidines are 2' F.

<400> SEQUENCE: 15
gggaggacga ugcggucaac cauccaacuu aagcugagaa aggaaccaca agccccagac    60
gacucgcccg    70

<210> SEQ ID NO 16
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 16
gggaggacga ugcggucaac cauccaacuc aagcugagaa aggaaccacu cgccccagac    60
gacucgcccg    70

<210> SEQ ID NO 17
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 17
gggaggacga ugcggauuga ucaaccaucc agcaagcuga gaaaggaacc aaccucagac    60
gacucgcccg    70

<210> SEQ ID NO 18
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 18
gggaggacga ugcggaucua cgcacucgca aaagcaucaa auguguccgc cgccucagac    60
gacucgcccg    70

<210> SEQ ID NO 19
<211> LENGTH: 68
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(68)
<223> OTHER INFORMATION: All pyrimidines are 2' F.  N at positions
      24, 27, 30, 33, 34, 40, 42, 46, 51 and 52 can by any
      nucleotide.

<400> SEQUENCE: 19
gggaggacga ugcgguuaga caanugnacn aanngaaucn anccanuccc nnccagacga    60
cucgcccg                                                            68

<210> SEQ ID NO 20
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(69)
<223> OTHER INFORMATION: All pyrimidines are 2' F.

<400> SEQUENCE: 20
gggaggacga ugcggaaugu uuauucauag aacaggucu acucaucaca uccccagacg     60
acucgcccg                                                           69

<210> SEQ ID NO 21
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F. N at positions 27,
      28, 30, 31, 37, 40, 41, 48 and 53 can by any
      nucleotide.

<400> SEQUENCE: 21
gggaggacga ugcggaaugu uuuguunngn nauuacnaan nuuacugncu auncucagac    60
gacucgcccg                                                          70

<210> SEQ ID NO 22
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 22
gggaggacga ugcggcccca acgacagaac aacuccacaa cugugcaguc ccccgcagac    60
gacucgcccg                                                          70

<210> SEQ ID NO 23
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(69)
<223> OTHER INFORMATION: All pyrimidines are 2' F.

```
<400> SEQUENCE: 23
gggaggacga ugcggcccca acgacagaac aacucauaac ugugcagucc cccgcagacg      60
acucgcccg                                                             69

<210> SEQ ID NO 24
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 24
gggaggacga ugcggcauca gcauauaacg gacaacgagc auacauuuca cgcgccagac      60
gacucgcccg                                                            70

<210> SEQ ID NO 25
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 25
gggaggacga ugcggccaca ucacucucuc acucccauug aauacuuacc cuccccagac      60
gacucgcccg                                                            70

<210> SEQ ID NO 26
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimindines are 2' F.

<400> SEQUENCE: 26
gggaggacga ugcggauucc ccucuccugu guaaccuucc uucucuucac cuccucagac      60
gacucgcccg                                                            70

<210> SEQ ID NO 27
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 27
gggaggacga ugcggaaccc gggcagucca aucuuucagu cccacaucug cuccccagac      60
```
gacucgcccg                                                              70

<210> SEQ ID NO 28
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.   N at position
      48 can by any nucleotide.

<400> SEQUENCE: 28
gggaggacga ugcggcaaac cuccacaacc ugcgcaagcu ucccaucnuu cugcccagac      60
gacucgcccg                                                              70

<210> SEQ ID NO 29
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 29
gggaggacga ugcggacguc ucgguugagc ccuuacaauc auuucuguau gcccucagac      60
gacucgcccg                                                              70

<210> SEQ ID NO 30
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 30
gggaggacga ugcggacgaa gacccgaugg cccagagaaa ucucccacuc ugccccagac      60
gacucgcccg                                                              70

<210> SEQ ID NO 31
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2' F.

<400> SEQUENCE: 31
gggaggacga ugcggaagcc cuaagagaau agcccuugac gccuacuccc cugcccagac      60
gacucgcccg                                                              70

```
<210> SEQ ID NO 32
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(15)
<223> OTHER INFORMATION: All pyrimidines are 2' F.

<400> SEQUENCE: 32
gggaggacga ugcgg                                                    15

<210> SEQ ID NO 33
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(15)
<223> OTHER INFORMATION: All pyrimidines are 2' F.

<400> SEQUENCE: 33
cagacgacuc gcccg                                                    15
```

US 6,171,795 B1

NUCLEIC ACID LIGANDS TO CD40LIGAND

FIELD OF THE INVENTION

This invention is directed to a method for the generation of nucleic acid ligands having specific functions against target molecules using a method known as Systematic Evolution of Ligands by EXponential enrichment (SELEX). The invention is directed towards nucleic acid ligands of CD40ligand.

BACKGROUND OF THE INVENTION

CD40ligand (also known as CD154) is a member of the TNF family of molecules. It is a type II membrane protein (N-terminus intracellular and C-terminus extracellular) that is expressed on activated T cells. The human protein is 261 residues long and has a single N-linked carbohydrate moiety. Antibodies to CD154 have been shown to suppress T cell and antibody mediated immune responses in a number of experimental systems. These include inhibition of graft rejection and blocking autoimmune disorders (Durie, F. H. et al. 1993. Science 261:1328). The combined use of anti-CD40ligand antibodies and CD28 blockers (i.e. CTLA-4Ig) has been shown to be effective in blocking graft rejection in both murine and rhesus transplant models (Larsen, C. P. et al. 1996. Nature 381: 434; Kirk, A.D. 1997. Proc. Natl. Acad. Sci. 94:8789). More recently, the use of anti-CD40ligand antibody as a single agent in rhesus kidney allografts has shown that this treatment is remarkably efficacious (Kirk, A. D. et al. 1999. Nature Medicine 5: 686.).

CD40ligand is also expressed on activated platelets and this observation has kindled interest in the role of CD40ligand-CD40 interactions in vascular biology (Henn, V. et al. 1998. Nature 391:591). CD40 and CD40 ligand expression has also been reported on vascular endothelium and smooth muscle cells (Mach, F. et al. 1997. Proc. Natl. Acad. Sci. 94:1931). One report has suggested that inhibition of CD40ligand:CD40 interactions may diminish the development of atherosclerotic lesions (Mach, F. et al. 1998. Nature 394: 200). Atherosclerosis has been viewed as a disease state in which inflammatory processes of the immune system may play a role. Given the potential therapeutic results of inhibiting the activity of the CD40ligand, it would be desirable to have high affinity and high specificity inhibitors of this molecule.

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", U.S. Pat. No. 5,270,163 (see also WO 91/19813) entitled "Methods For Identifying Nucleic Acid Ligands", each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8, 1998, entitled "Systematic Evolution of Ligands by Exponential Enrichment: Photoselection of Nucleic Acid Ligands and Solution SELEX", describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-NH2), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleotides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide fictional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes". Each of the above described patent applications which describe modifications of the basic SELEX procedure are specifically incorporated by reference herein in their entirety.

It is an object of the present invention to provide methods that can be used to identify nucleic acid ligands that bind with high specificity and affinity to CD40ligand.

It is a further object of the present invention to obtain nucleic acid ligands to CD40ligand that inhibit the activity of CD40ligand when bound.

SUMMARY OF THE INVENTION

The present invention describes a method for isolating nucleic acid ligands that bind to human CD40ligand with high specificity. The method uses the SELEX process for the Systematic Evolution of Ligands by EXponential enrichment. The nucleic acid ligands of the invention can inhibit the interaction of CD40ligand with its receptor CD40. High affinity nucleic acid ligands to CD40ligand can have many potential uses in diseases of the immune system.

DETAILED DESCRIPTION OF THE PREFERRED EMBODIMENTS

Figure 1:
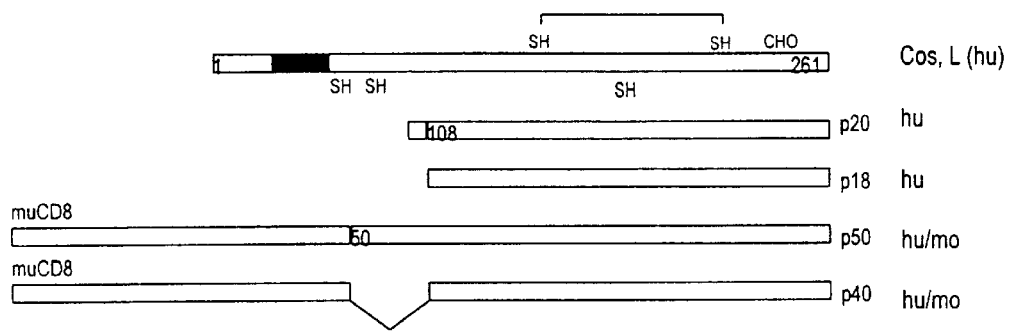
FIG. 1 shows the structure of the CD40ligand proteins used as SELEX targets in the instant invention.

The central method utilized herein for identifying nucleic acid ligands to CD40ligand is called the SELEX process, an acronym for Systematic EEvolution of Ligands by Exponential enrichment and involves (a) contacting the candidate mixture of nucleic acids with CD40ligand, or expressed domains or peptides corresponding to CD40ligand, (b) partitioning between members of said candidate mixture on the basis of affinity to CD40ligand, and (c) amplifying the selected molecules to yield a mixture of nucleic acids enriched for nucleic acid sequences with a relatively higher affinity for binding to CD40ligand.

Definitions

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are often referred to as "aptamers". A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the present invention, the target is CD40ligand, or regions thereof. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping. "SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to CD40ligand.

The SELEX methodology is described in the SELEX Patent Applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX target is CD40ligand. In particular, the SELEX targets in this application include purified CD40ligand, and fragments thereof, and short peptides or expressed protein domains comprising CD40ligand. Also included as targets are fusion proteins comprising portions of CD40ligand and other proteins, such as murine CD8.

As used herein, "solid support" is defined as any surface to which molecules may be attached through either covalent or non-covalent bonds. This includes, but is not limited to, membranes, microtiter plates, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

As used herein "CD40ligand" refers to the ligand for CD40. "CD40ligand" also refers to CD154. This includes purified ligand, fragments of ligand, chemically synthesized fragments of the ligand, derivatives or mutated versions of the ligand, and fusion proteins comprising the ligand and another protein. "CD40ligand" as used herein also includes the ligand of the CD40 receptor isolated from a species other than humans.

Note, that throughout this application various citations are provided. Each citation is specifically incorporated herein in its entirety by reference.

A. Preparing Nucleic Acid Ligands to CD40ligand.

In the preferred embodiment, the nucleic acid ligands of the present invention are derived from the SELEX methodology. The SELEX process is described in U.S. patent application Ser. No. 07/536,428, entitled Systematic Evolution of Ligands by Exponential Enrichment, now abandoned, U.S. Pat. No. 5,475,096, entitled Nucleic Acid Ligands and, U.S. Pat. No. 5,270,163 (see also WO 91/19813) entitled Methods for Identifying Nucleic Acid. These applications, each specifically incorporated herein by reference, are collectively called the SELEX Patent Applications.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8 1998, entitled "Systematic Evolution of Ligands by Exponential Enrichment: Photoselection of Nucleic Acid Ligands and Solution SELEX", all describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938 entitled "Nucleic Acid Ligands to HIV-RT and HIV-1 Rev," describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-NH2), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement, " now abandoned describes oligonucleotides containing various 2' modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by Exponential Enrichment: Chimeric SELEX," and U.S. Pat. No. 5,683,867 entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938, methods are described for obtaining improved nucleic acid ligands after the SELEX process has been performed. This patent, entitled Nnucleic Acid Legands to HIV-RT and HIV-I Rev, is specifically incorporated herein by reference.

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 9, 1993, now abandoned, and U.S. Pat. No. 5,660,985, both entitled "High Affinity Nucleic Acid Ligands Containing Modified Nucleotides", and the U.S. Patent Application entitled "Transcription-free SELEX", U.S. patent application Ser. No. 09/362,578, filed Jul. 28, 1999, each of which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The nucleic acid ligands of the invention are prepared through the SELEX methodology that is outlined above and thoroughly enabled in the SELEX applications incorporated herein by reference in their entirety. The SELEX process can be performed using purified CD40ligand, or fragments thereof as a target. Alternatively, full-length CD40ligand, or discrete domains of CD40ligand, can be produced in a suitable expression system. Alternatively, the SELEX process can be performed using as a target a synthetic peptide that includes sequences found in CD40ligand. Determination of the precise number of amino acids needed for the optimal nucleic acid ligand is routine experimentation for skilled artisans.

In some embodiments, the nucleic acid ligands become covalently attached to their targets upon irradiation of the nucleic acid ligand with light having a selected wavelength. Methods for obtaining such nucleic acid ligands are detailed in U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8 1998, entitled "Systematic Evolution of Ligands by Exponential Enrichment: Photoselection of Nucleic Acid Ligands and Solution SELEX" each of which is specifically incorporated herein by reference in its entirety.

In preferred embodiments, the SELEX process is carried out using fragments of CD40ligand that are bound to magnetic beads through hydrophobic interactions. A candidate mixture of single stranded RNA molecules is then contacted with the magnetic beads in the wells of a microtiter plate. After incubation for a predetermined time at a selected temperature, the beads are held to the sides of the wells of the plate by a magnetic field, and the wells of the plate are washed to remove unbound candidate nucleic acid ligands. The nucleic acid ligands that bind to the CD40ligand are then released into solution in the wells, then reverse transcribed by reverse transcriptase and amplified using the Polymerase Chain Reaction. The amplified candidate mixture is then used to begin the next round of the SELEX process.

The nucleic acid ligands isolated by the method of the present invention can then be tested for binding to CD40ligand protein and for inhibition of the interaction between CD40ligand and CD40. This can be done, for example, by assaying the nucleic acid ligand for inhibition of the proliferation of B cells that is normally induced by CD40ligand and IL-4. Alternatively, the nucleic acid ligands, and CD40ligand or a CD40ligand-fusion protein, can added to cells positive for the CD40 protein, and the inhibition of the interaction can be seen by immunofluorescence using an antibody directed towards an irrelevant portion of the protein, such as murineCD8 in a murineCD8-humanCD40ligand fusion protein. Inhibition of the interaction between soluble CD40ligand and CD40 expressed at the cell surface results in diminished fluorescent staining at the cell surface, or none at all.

B. Diagnostic and Therapeutic Applications of CD40ligand Nucleic Acid Ligands

The nucleic acid ligands provided by the instant invention are useful in a number of medical applications. For example, they can be used to treat or diagnose any disease in which T cell activity, antibody-mediated immune responses, or activated platelets play a role in pathogenesis. In some embodiments, they can used in patients who have received an organ transplant or a graft in order to block organ or graft rejection. In other embodiments, the nucleic acid ligands are used to reduce the development of vascular diseases, such as the development of atherosclerotic lesions. In still further embodiments, the nucleic acid ligands are used to treat autoimmune disorders. In order to use nucleic acid ligands as therapeutic agents, it may be necessary to use modified nucleotides and ribonucleotides in order to impart increased stability upon the nucleic acid ligand in biological fluids. Such modifications are described above in the SELEX patent applications.

The nucleic acid ligands of the instant invention can also be used to image blood clots formed by platelet aggregation. Patients susceptible to thrombosis—because of major trauma or surgery—can be injected with radiolabelled nucleic acid ligands to CD40ligand, and then radioimaging can reveal sites in the body where large aggregations of platelets, and hence thrombi, are present. If a thrombosis is detected at a critical site in the body, then anticoagulant and thrombolytic treatment can be given locally. The advantage of using such a nucleic acid ligand imaging agent is that the anticoagulant and thrombolytic treatments—which can cause harm if administered prophylactically by allowing internal bleeding to continue without efficient clotting—can be given only to those individuals who definitely have a dangerous thrombosis. Moreover, these treatments can be specifically injected at the site where the thrombosis has been detected by the nucleic acid ligands of the instant invention, instead of injecting higher concentrations into the bloodstream in the hope that some active agent will be carried to all potential sites of thrombosis.

EXAMPLES

The following examples are given by way of illustration only. They are not to be taken as limiting as the scope of the present invention in any way.

Example 1

Generation of CD40ligand for Use as Target in the SELEX Process

CD40ligand was expressed in *E. Coli* as a fusion protein. The fusion protein comprised amino acid 108 to amino acid 261 (the carboxy terminus) of human CD40ligand fused at the $NH_2$-terminus to a 6-his sequence followed by a thrombin cleavage site. The resulting fusion protein, p20, was purified by binding to a Ni-NTA column. p18 was then generated by treatment of p20 with biotinylated thrombin, followed by removal of the biotinylated thrombin with streptavidin agarose followed by dialysis.

CD40ligand was also expressed in eukaryotic cells—both COS and CHO cells—as a murineCD8-humanCD40ligand fusion protein. The resulting protein, p40/p50 was purified by anti CD8-Sepharose chromatography. A variant of this construct (p40) contains an internal deletion which removes residues 50–108 of the CD40ligand protein; this eliminates two free cysteine residues and results in a protein with a reduced level of intermolecular crosslinking.

In addition, to the proteins described above, human CD40ligand was expressed in transfected L cells using a full length cDNA encoding the mature CD40ligand protein. The structure of the various expressed CD40ligand proteins is shown in FIG. 1.

The p18 and p40/p50 proteins were demonstrated to have biological activity. p18 was able to induce B cell proliferation in the presence of IL-4. This proliferation was inhibited by anti-CD40ligand antibodies. This shows that the B cell proliferative activity was not due to bacterial lipopolysaccharides; in addition, a control protein (6-his-beta-galactosidase) purified in a similar manner did not have B cell proliferative activity. The p40/p50 was also shown to stimulate B cell proliferation in the presence of IL-4. In addition, p40/p50 was shown to bind to CD40-positive Raji cells and normal B cells by use of a secondary reagent directed to the CD8 portion of the molecule (see FIG. 2).

Example 2

Generating Nucleic Acid Ligands to p18 and p40

The SELEX method was performed using both p18 and p40 proteins which were bound to magnetic beads by hydrophobic absorption. The beads were contacted with a candidate mixture of single stranded RNA, and incubated to allow the candidate nucleic acid ligands to bind to the p18 or p40 protein immobilized on the beads. The beads were then washed to remove unbound candidate nucleic acid ligands, and the beads were partitioned from the unbound nucleic acid ligands by applying a magnetic field. The nucleic acid ligands that bound to p18 or p40 were then eluted from the beads. The eluted nucleic acid ligands were reverse transcribed, and the resulting DNA templates were amplified using the polymerase chain reaction. The amplified DNA templates were then transcribed to yield a candidate mixture of nucleic acid ligands enriched for nucleic acid ligands that bind to p18 or p40. This process was repeated for a total of 6 rounds.

The progress of the different SELEX rounds is shown in TABLE 1. After six rounds nucleic acid ligand pools were tested in several assays. RNA from Round 6 of the p40 SELEX experiment was used to bind to muCD8-humanCD40 ligand fusion protein; the binding data revealed that affinity for the Round 6 pool had improved ~2 logs relative to the Round 0 unselected pool. Binding to an irrelevant CD8 fusion protein was negligible.

clature indicates the protein target (p18 or p40), the SELEX Round the nucleic acid ligand was obtained from, and the final number indicates the clone identification number.

TABLE 1

SELEX parameter and results for 6 rounds of the SELEX method using p18 and p40.

Magnetic Bead Selex-CD40 ligand
concentration of protein on beads determined by Micro 8CA assay

| P40 | 125 nM | 2.25 ug/ml | mw = 40 kD |
| P18 | 104 nM | 4.14 ug/ml | mw = 18 kD | binding buffer = Hepes buffered saline pH 7.4, 0.01% HSA, 0.05% tween 2D
library = 2'F pyrimidine 40N7
reaction volume = 100 ul
0.6% bead solids

| Round | fold decrease target | bead volume | [protein] | [RNA](uM) | RNA/protein | fold decrease RNA bound | molecules RNA bound | background | S/N(QPCR) |
|---|---|---|---|---|---|---|---|---|---|
| P18 | | | | | | | | | |
| 1 | | 50 | 6.25E-08 | 2.9 | 46 | | 1.20E+11 | 2.80E+08 | 429 |
| 2 | 3 | 16.7 | 2.10E-08 | 1.95 | 93 | 1.25 | 9.60E+10 | 2.70E+07 | 3556 |
| 3 | 5.6 | 3 | 3.75E-09 | 2 | 533 | 6.9 | 1.40E+10 | 1.10E+08 | 127 |
| 4 | 5 | 0.6 | 7.50E-10 | 2 | 2667 | 5.8 | 2.40E+09 | 1.00E+09 | 2.4 |
| 5 | 2 | 0.3 | 3.75E-10 | 1.5 | 4000 | 4 | 5.80E+08 | 3.40E+07 | 17 |
| 6 | 3 | 0.1 | 1.25E-10 | 2.5 | 20000 | 1 | 5.60E+08 | 3.70E+07 | 15 |
| P40 | | | | | | | | | |
| 1 | | 50 | 5.20E-08 | 2.9 | 56 | | 1.40E+09 | 2.80E+08 | 5 |
| 2 | 0 | 50 | 5.20E-08 | 1.95 | 38 | 2.2 | 6.40E+08 | 1.30E+08 | 5 |
| 3 | 2 | 25 | 2.60E-08 | 2 | 77 | 77 increase | 4.90E+10 | 2.50E+08 | 196 |
| 4 | 5 | 5 | 5.20E-09 | 2 | 385 | 2.7 | 1.80E+10 | 1.60E+07 | 1125 |
| 5 | 10 | 0.5 | 5.20E-10 | 3 | 5770 | 46 | 3.90E+08 | 8.30E+07 | 5 |
| 6 | 2 | 0.25 | 2.6E-10 | 2.5 | 9615 | 1 | 4.00E+08 | 3.50E+07 | 11 |

Example 3

Sequences of Clones Obtained from the SELEX Method Using p40 and p18 as Targets

The sequences of the clones from the p40 SELEX and the p18 SELEX are shown in Table 2 and Table 3. The nomenclature indicates the protein target (p18 or p40), the SELEX Round the nucleic acid ligand was obtained from, and the final number indicates the clone identification number. Hence, p40R6.3 indicates clone number 3 obtained from round 6 of the SELEX experiment using p40 as a target. Note that each aptamer shown in Tables 2 and 3 has the 30 N7 fixed sequence gggaggacgaugcgg (SEQ ID NO:32) at the 5' end, and the 30N7 fixed sequence cagacgacucgcccg (SEQ ID NO:33) at the 3' end.

TABLE 2

Aptamer sequences derived from Round 6 of SELEX to murineCD8-human CD40ligand fusion protein. Each aptamer has 30N7 fixed sequences at the 5' and 3' ends.

| | | |
|---|---|---|
| P40R6.3 | ctcgagaaaggaacaaaggtcaaccatccgagccctaccn | SEQ ID NO:1 |
| P40R6.9 | ctcgagaaaggaacaaaggtcaaccatccgagccctacca | SEQ ID NO:2 |
| P40R6.1 | ctcgagaaaggaacaaaggtcaaccatccgagccctacca | SEQ ID NO:3 |
| P40R6.13 | ctcgagaaaggaacaaaggtcaaccatccgagcccaacct | SEQ ID NO:4 |
| P40R6.17 | ctcgagaaaggaacaaaggtcaaccatccgagccctaccc | SEQ ID NO:5 |
| P40R6.29 | attgcgagaaaggagcctcttaagaccaaccatccgcc | SEQ ID NO:6 |
| P40R6.34 | caagaaaggaacgttcagtcaaccatctgctaccgctccc | SEQ ID NO:7 |
| P40R6.44 | caagaaaggaacgttcagtcaaccatctgctaccgccccc | SEQ ID NO:8 |

TABLE 2-continued

Aptamer sequences derived from Round 6 of SELEX to murineCD8-human CD40ligand fusion protein. Each aptamer has 30N7 fixed sequences at the 5' and 3' ends.

| | | |
|---|---|---|
| P40R6.48 | agaaaggaagaactctctcaaccatcccacaccagccccc | SEQ ID NO:9 |
| P40R6.2 | caactctcgagaaaggaacatcaaagtgtcaaccatccgt | SEQ ID NO:10 |
| P40R6.19 | cctaagaaaggaatttaaaccaatcaaccatctagaaccc | SEQ ID NO:11 |
| P40R6.28 | gcctcgagaaag-aaccatacagggtaatcatccgttcgcc | SEQ ID NO:12 |
| P40R6.4 | tcaaccatccaactcaag ttgagaaaggaaccactagccc | SEQ ID NO:13 |
| P40R6.7 | tcaaccatccaactcaagttgagaaaggaaccactacccc | SEQ ID NO:14 |
| P40R6.25 | tcaaccatccaacttaagctgagaaaggaaccacaagccc | SEQ ID NO:15 |
| P40R6.30 | tcaaccatccaactcaagctgagaaaggaaccactcgccc | SEQ ID NO:16 |
| P40R6.16 | attgatcaaccatccagcaagctgagaaaggaaccaacct | SEQ ID NO:17 |
| P40R6.8 | atctacgcactcgcaaaagcatcaaatgtgtccgccgcct | SEQ ID NO:18 |
| P40R6.40 | ttagacaantgnacnaanngaatcnanccantcccnnc | SEQ ID NO:19 |

TABLE 3

Aptamer sequences derived from Round 6 of SELEX to p18-E. Coli produced CD40ligand. Each aptamer has 30N7 fixed sequences at the 5' and 3' ends.

| | | |
|---|---|---|
| P18R6.7 | aatgtttattcatagaacagggtctactcatcacatccccc | SEQ ID NO:20 |
| P18R6.22 | aatgttttgttnngnnattacnaannttactgnctatnct | SEQ ID NO:21 |
| P18R6.14 | ccccaacgacagaacaactccacaactgtgcagtcccccg | SEQ ID NO:22 |
| P18R6.17 | ccccaacgacagaacaactcataactgtgcagtcccccg | SEQ ID NO:23 |
| P18R6.11 | catcagcatataacggacaacgagcatacatttcacgcgc | SEQ ID NO:24 |
| P18R6.3 | ccacatcactctctcactcccattgaatacttaccctccc | SEQ ID NO:25 |
| P18R6.5 | attcccctctcctgtgtaaccttccttctctcacctcct | SEQ ID NO:26 |
| P18R6.2 | aacccgggcagtccaatctttcagtcccacatctgctccc | SEQ ID NO:27 |
| P18R6.1 | caaacctccacaacctgcgcaagcttcccatcnttctgcc | SEQ ID NO:28 |
| P18R6.21 | acgtctcggttgagcccttacaatcatttctgtatgccct | SEQ ID NO:29 |
| P18R6.9 | acgaagacccgatggcccagagaaatctcccactctgccc | SEQ ID NO:30 |
| P18R6.15 | aagccctaagagaatagcccttgacgcctactcccctgcc | SEQ ID NO:31 |

Example 4
Inhibition of the Binding of the MurineCD8-humanCD40ligand Fusion Protein to CD40-positive Cells RNA from Round 6 for the p 18 (p 18R6 pool) and p40 SELEX experiments was prepared and tested for its ability to inhibit the binding of the murineCD8-humanCD40ligand fusion to CD40-positive cells (as revealed by binding of fluorescent anti-CD8-PE antibody to the cells). MurineCD8-humanCD40ligand (mCD8-hCD40ligand) at a concentration of 0.25 µg/ml was incubated with 1×10 e-5 Raji cells (CD40-positive) and incubated for 1 hr at room temperature followed by three washes and subsequent incubation with anti-mCD8-PE antibody (obtained from Pharmingen). At this concentration of mCD8-huCD40ligand, a mean channel fluorescence (MCF) value of ~8 was obtained (see FIG. 2). Inhibition of this interaction was performed as follows: nucleic acid ligands, antibodies, and Ig fusions (humanCD40-human Ig and human CD5-human Ig) were incubated with the indicated concentrations with 0.25 μg/ml of mCD8-hCD40ligand in a 50ul reaction for ½ hr at 37° C. followed by the addition of Raji cells (1×105) cells. The incubation was continued at 37° C. for 1 hr followed by three washes with PFA (PBS; 10% Fetal Calf Serum; Na Azide 0.01%). The cells were then incubated in PFA containing fluorescently-labelled anti-murine CD8 antibody (PE anti-mCD8) for 1 hr. and washed three times prior to analysis by Fluorescence Activated Cell Sorting (FACS) using a Coulter Facstar.

Figure 2:
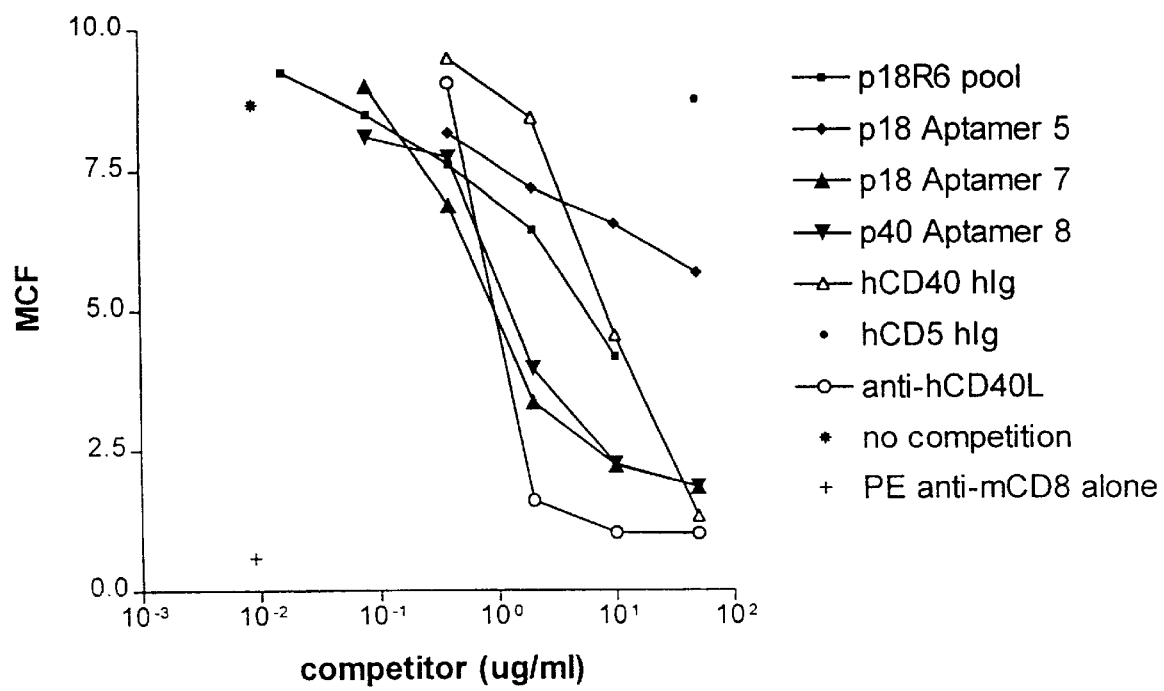
FIG. 2 shows inhibition of binding of a murineCD8-human CD40ligand fusion protein to the surface of Raji cells (CD40-positive) by nucleic acid ligands to CD40ligand.

Clones from each of the SELEX pools were also analyzed. Two round 6 clones, p40R6.8 (p40 Aptamer 8) and p18R6.7 (p18 Aptamer 7), were found to be strong inhibitors of the CD40ligand interaction (see FIG. 2). These nucleic acid ligands were unable to inhibit the binding of murine p40 (murineCD8-murine CD40ligand) (data not shown), demonstrating that the nucleic acid ligand does not bind to the CD8 sequence and is not crossreactive with murine CD40ligand. Also shown in FIG. 2 are the binding curves for p18R6.5 (p18 aptamer 5), the entire round 6 pool for the p18 SELEX experiment (p18R6 pool), human CD40-human Ig fusion protein (hCD40 hIg), human CD5-human Ig fusion protein (hCD5 hIg), anti-humanCD40ligand antibody (anti-hCD40L), and anti-murineCD8 antibody (PE anti-mCD8).

The inhibitory aptamers (p40R6.8, p18R6.7) represented ~10–15% of the sequences obtained. Binding analysis using the p40R6.8 aptamer give an affinity of the aptamer for the p40 protein of ~200pM; however, the binding curve is biphasic and the plateau RNA binding is poor (~15%).

Example 5

Staining of Ltk Cells with Biotinylated Nuclei Acid Ligands

Figure 3:
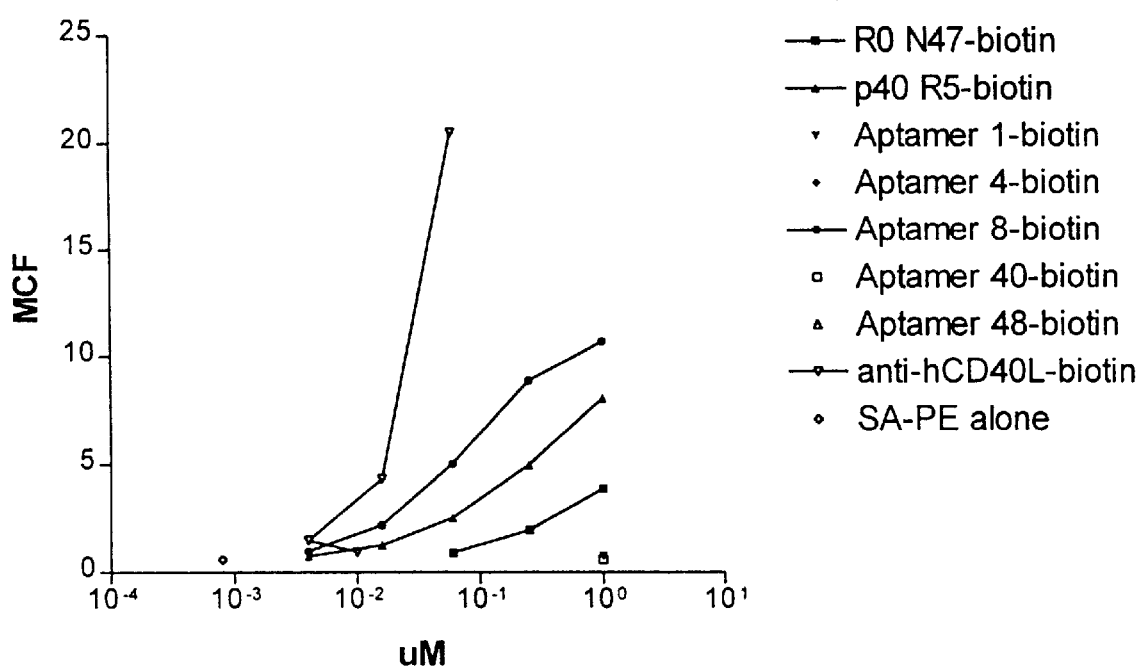
FIG. 3 illustrates the binding of biotinylated CD40ligand nucleic acid ligands to Ltk cells expressing the human CD40ligand gene.

Ltk cells were transfected for expression of the human CD40ligand gene; clone #279 was selected for high level constitutive expression. These cells were incubated with biotinylated nucleic acid ligands at the concentrations indicated in FIG. 3. The biotinylated p40 nucleic acid ligands used were: round 5 nucleic acid ligands (p40 R5-biotin), p40 R6.1 (Aptamer 1 -biotin), p40R6.4 (Aptamer 4-biotin), p40R6.8 (Aptamer-8 biotin), p40R6.40 (Aptamer 40-biotin) and p40R6.48 (Aptamer 48-biotin). The initial candidate mixture (RO N47-biotin) was also assayed. Anti-human CD40ligand antibody (anti-hCD40L-biotin) (obtained from Pharmingen) was used as a control. After incubation for ½ hrs at 4° C., the cells were washed once and incubated with fluorescently-labelled streptavidin (SA-PE) for 1 hr at 4° C. Cells were washed three times in PFA and analyzed. The results (FIG. 3) show that biotinylated aptamers are able to bind to humanCD40ligand transfectants.

What is claimed is:

1. A nucleic acid ligand to CD40ligand identified according to a method comprising:

a) preparing a candidate mixture of nucleic acids;

b) contacting the candidate mixture of nucleic acids with CD40ligand, wherein nucleic acids having an increased affinity to CD40ligand relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acids with relatively higher affinity and specificity for binding to CD40ligand, whereby a nucleic acid ligand of CD40ligand may be identified.

2. The nucleic acid ligand of claim 1 wherein said CD40ligand is associated through hydrophobic interactions with a solid support, and wherein steps b)–c) take place on the surface of said solid support.

3. The nucleic acid of claim 2 wherein said solid support is a bead.

4. The nucleic acid ligand of claim 1 wherein said candidate mixture of nucleic acids is comprised of single stranded nucleic acids.

5. The nucleic acid ligand of claim 4 wherein said single stranded nucleic acids are ribonucleic acids.

6. The nucleic acid ligands of claim 4 wherein said single stranded nucleic acids are deoxyribonucleic acids.

7. The nucleic acid ligand of claim 5 wherein said candidate mixture of nucleic acids comprises 2'-F (2'-fluoro) modified ribonucleic acids.

8. A purified and non-naturally occuring RNA ligand to CD40ligand wherein said ligand is selected from the group consisting of SEQ. ID. NO. 18, 20 and 26.

9. A purified and non-naturally occurring nucleic acid ligand to CD40ligand.

10. The purified and non-naturally occurring nucleic acid ligand of claim 3 wherein said nucleic acid ligand is single stranded.

11. The purified and non-naturally occurring nucleic acid ligand of claim 10 wherein said nucleic acid ligand is RNA.

12. The purified and non-naturally occurring RNA ligand of claim 11 wherein said ligand is comprised of 2'-fluoro (2'-F) modified nucleotides.

13. A method of inhibiting interaction of CD40ligand and CD40 positive cells in vitro comprising contacting the CD40ligand with a CD40ligand nucleic acid ligand.

14. The method of claim 13 wherein the CD40ligand nucleic acid ligand has been modified to improve its resistance to degradation.

* * * * *